United States Patent [19]

Schach et al.

[11] Patent Number: 6,114,589
[45] Date of Patent: Sep. 5, 2000

[54] PROCESS FOR THE PREPARATION OF FLUORINATED AROMATIC COMPOUNDS

[75] Inventors: Thomas Schach, Gernsheim; Thomas Wessel, Frankfurt; Maren Gutermuth, Bensheim, all of Germany

[73] Assignee: Clariant GmbH, Frankfurt, Germany

[21] Appl. No.: 09/170,381

[22] Filed: Oct. 13, 1998

[30] Foreign Application Priority Data

Oct. 13, 1997 [DE] Germany .................. 197 45 212

[51] Int. Cl.$^7$ .................................................. C07C 205/12
[52] U.S. Cl. .................. 568/938; 570/127; 570/141; 570/170; 502/150; 502/164
[58] Field of Search .................. 502/164, 150, 502/162, 208; 568/938, 433, 437; 570/127, 141, 170

[56] References Cited

U.S. PATENT DOCUMENTS

| | | | |
|---|---|---|---|
| 3,123,614 | 3/1964 | Yale et al. | 260/296 |
| 3,414,905 | 12/1968 | O'Brien et al. | 346/33 |
| 4,069,262 | 1/1978 | Kunz | 260/646 |
| 4,226,811 | 10/1980 | Oeser et al. | 568/937 |
| 5,466,859 | 11/1995 | Schach et al. | 558/425 |
| 5,476,976 | 12/1995 | Schach et al. | 568/938 |
| 5,492,875 | 2/1996 | Schach et al. | 502/164 |
| 5,502,260 | 3/1996 | Schach et al. | 568/938 |

FOREIGN PATENT DOCUMENTS

| | | |
|---|---|---|
| 0146924 | 7/1985 | European Pat. Off. . |
| 0635303 | 1/1995 | European Pat. Off. . |
| 0635481 | 1/1995 | European Pat. Off. . |
| 0635482 | 1/1995 | European Pat. Off. . |
| 0635486 | 1/1995 | European Pat. Off. . |

OTHER PUBLICATIONS

Speciality Chemicals, Ed. Brian Pearson, Elsevier 1991, p. 15–77.
R. Schwesinger et al, Angew. Chem. 103 (1991) p. 1376.
R. Schwesinger et al, Chem. Ber. 127 (1994) p. 2435–2454.

*Primary Examiner*—Johann Richter
*Assistant Examiner*—Sreeni Padmanabhan
*Attorney, Agent, or Firm*—Scott E. Hanf

[57] ABSTRACT

The invention relates to a process for the preparation of fluorinated compounds $$Az_xArF_wCl_{(y-w)}R_z \quad (1)$$

in which Az is a radical —F, —Cl, —Br, —NO$_2$, —CN, —CF$_3$, —CCl$_3$, —CHO, —CO(C$_n$H$_{2n+1}$), —COX or —SO$_2$X, where X is F, Cl or Br, x is an integer from 1 to 3, Ar is a phenyl radical, pyridyl radical or naphthyl, w is an integer from 1 to y, y is an integer from 1 to 5, R is H, an alkyl radical or an alkoxy radical having from 1 to 10 carbon atoms, z is an integer from 1 to 5, (x+y+z) is the number of all substitutable valences on the radical Ar, which comprises reacting a compound $$Az_xArCl_yR_z \quad (2),$$

with an alkali metal fluoride in the presence of a component a) or a mixture of component a) and at least one of components b), c), d) and/or e), component a) being one or more quaternary ammonium compounds which contain one or more radicals —(C$_m$H$_{2m}$O)R$^5$, component b) being an amidophosphonium salt, component c) being a quaternary ammonium salt, component d) being a quaternary phosphonium salt, component e) being a polyether, and carrying out the reaction at from 50 to 250° C., removing the compound of the formula (1) formed during the reaction by distillation, and the compound of the formula (2) is fed to the reaction mixture at a rate corresponding to the rate at which the compound of the formula (1) is removed.

21 Claims, No Drawings

PROCESS FOR THE PREPARATION OF FLUORINATED AROMATIC COMPOUNDS

CROSS REFERENCES TO RELATED APPLICATIONS

The present invention is described in the German priority application No. 19745212.4, filed Oct. 13, 1997, which is hereby incorporated by reference as is fully disclosed herein.

BACKGROUND OF THE INVENTION

The present invention relates to a novel process for the preparation of fluorinated aromatic compounds which makes the desired compounds accessible by halogen-fluorine exchange in a gentle manner.

Fluorinated aromatic compounds, in particular fluorobenzene and fluorobenzene derivatives, play an important role as intermediates in the preparation of crop-protection compositions (herbicides) and are the synthesis building blocks for pharmaceuticals, for example for the preparation of quinolonecarboxylic acids (Speciality Chemicals, Ed. Brian Pearson, Elsevier 1991, pages 15 to 77) and can also be used as precursors in the preparation of dyes.

Replacement of a halogen, preferably of chlorine or bromine in activated aromatic chlorine or bromine compounds, by fluorine is a favorable method of introducing fluorine substituents into an aromatic system. This reaction is generally carried out in the presence of dipolar aprotic solvents, which are used in comparatively large amounts, and alkali metal fluorides as a source of fluoride (U.S. Pat. No. 4,226,811, U.S. Pat. No. 4,069,262).

Die EP-A-0 146 924 relates to a process for the preparation of a beta-fluoropyridine compound by reacting an alpha- or gamma-halosubstituted β-halopyridine with KF or CsF in a polar aprotic solvent, the beta-fluoropyridine product essentially being removed as soon as it forms and, where appropriate, the alpha- or gamma-halo-substituted β-halopyridine being added. The reaction can be carried out in the presence of a phase transfer catalyst, although it can also proceed, as most of the examples show, in the absence of a phase transfer catalyst. The disadvantage of the process is that it is limited to certain fluoropyridines and requires large amounts of the polar aprotic solvent.

More recently, solvent-free processes have also become known. These solvent-free processes are carried out in the presence of phase transfer catalysts. Catalysts which have proven particularly advantageous are, for example, quaternary ammonium compounds or quaternary phosphonium compounds.

EP-A-0 635 303 describes a catalyst mixture which comprises a quaternary ammonium compound substituted by at least one alkoxypolyoxyalkyl radical, and also one or more quaternary ammonium salts and/or phosphonium salts and/or polyethers or crown ethers.

The quaternary ammonium compounds substituted by at least one alkoxypolyoxyalkyl radical, which correspond to component a) specified below, are either used alone or in the form of the catalyst mixtures described above for the preparation of fluoronitrobenzenes (EP-A-0 635 481), for the preparation of polyfluorinated nitrobenzenes (EP-A-0 635 482) or for the preparation of fluoronitrobenzenes (EP-A-0 635 486).

Although the yields which can be obtained using the process described above are relatively good, they are sometimes achieved at the expense of very long reaction times. The resulting low space-time yields are very disadvantageous for an industrial process since they make the industrial production considerably more expensive.

SUMMARY OF THE INVENTION

The object is thus to provide a process which, firstly, is suitable for the preparation of a large number of fluorinated aromatic compounds and is easy to carry out industrially and, secondly, avoids the disadvantages of long reaction times and low space-time yields.

DESCRIPTION OF THE PREFERRED EMBODIMENTS

This object is achieved by a process for the preparation of fluorinated compounds of the formula (1)

$$Az_xArF_wCl_{(y-w)}R_z \qquad (1)$$

in which Az independently of one another are identical or different and are a radical —F, —Cl, —Br, —NO$_2$, —CN, —CF$_3$, —CCl$_3$, —CHO, —CO(C$_n$H$_{2n+1}$), where n is an integer from 1 to 10, —COX or —SO$_2$X, where X is F, Cl or Br, x is an integer from 1 to 3, Ar is a phenyl radical, pyridyl radical or naphthyl radical, w is an integer from 1 to y, y is an integer from 1 to 5, R independently of one another are identical or different and are H, a straight-chain or branched alkyl radical having from 1 to 10 carbon atoms or a straight-chain or branched alkoxy radical having from 1 to 10 carbon atoms, z is an integer from 1 to 5, where (x+y+z) is the number of all substitutable valences on the radical Ar.

It comprises reacting a compound of the formula (2)

$$Az_xArCl_yR_z \qquad (2)$$

in which Az, x, Ar, y, R, z and (x+y+z) are as defined for formula 1, with an alkali metal fluoride or a mixture of alkali metal fluorides in the presence of a component a) or a mixture of component a) and at least one of components b), c), d) and e), component a) being one or more quaternary ammonium compounds of the formula (3)

$$R^2-\overset{R^1}{\underset{R^4}{N^{\oplus}}}-R^3 \quad X^{\ominus} \qquad (3)$$

in which
R$^1$, R$^2$ and R$^3$ are identical or different and are a straight-chain or branched radical of the formula —(C$_m$H$_{2m}$O)$_p$R$^5$, in which R$^5$ is hydrogen or a straight-chain or branched alkyl radical having from 1 to 16 carbon atoms, m is an integer from 1 to 10 and p is a number from 1 to 15; or a straight-chain or branched alkyl radical having from 1 to 30 carbon atoms;
or an unsubstituted phenyl or naphthyl radical; or a substituted phenyl or naphthyl radical where the substituents are halogen, C$_{1-C4}$-alkyl, C$_1$–C$_4$-alkoxy, nitro or cyano;
R$^4$ is a straight-chain or branched radical of the formula —(C$_m$H$_{2m}$O)$_p$R$^5$; and
X$^{\ominus}$ is a monobasic acid radical or the equivalent of a polybasic acid radical,
component b) being one or more amidophosphonium salts of the formula (4)

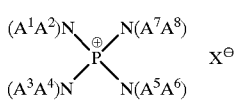

(4)

in which $A^1$, $A^2$, $A^3$, $A^4$, $A^5$, $A^6$, $A^7$, $A^8$ independently of one another are identical or different and are a straight-chain or branched alkyl or alkenyl having from 1 to 12 carbon atoms, cycloalkyl having from 4 to 8 carbon atoms, an aryl having from 6 to 12 carbon atoms, an aralkyl having from 7 to 12 carbon atoms, or $A^1A^2$, $A^3A^4$, $A^5A^6$ and $A^7A^8$ independently of one another are identical or different and are bonded together, directly or via O or N—$A^9$, to give a ring having from 3 to 7 ring members, $A^9$ is an alkyl having from 1 to 4 carbon atoms and $X^-$ is a monobasic acid radical or the equivalent of a polybasic acid radical, component c) being one or more quaternary ammonium compounds of the formula (5)

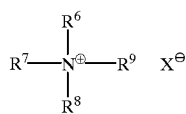

(5)

in which $R^6$, $R^7$, $R^8$ and $R^9$ are identical or different and are a straight-chain or branched alkyl radical having from 1 to 22 carbon atoms; or an unsubstituted or substituted aryl radical or a $C_1$–$C_4$-alkylaryl radical, where aryl is phenyl or naphthyl, and said substituents are halogen, $C_1$–$C_4$-alkyl, $C_1$–$C_4$-alkoxy, nitro or cyano; and $X^-$ is a monobasic acid radical or the equivalent of a polybasic acid radical;

component d) being one or more quaternary phosphonium compounds of the formula (6)

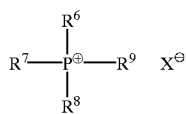

(6)

in which $R^6$, $R^7$, $R^8$ and $R^9$ are identical or different and are a straight-chain or branched alkyl radical having from 1 to 22 carbon 20 atoms;

or an unsubstituted or substituted aryl radical or a $C_1$–$C_4$-alkylaryl radical, where aryl is phenyl or naphthyl, and said substituents are halogen, $C_1$–$C_4$-alkyl, $C_1$–$C_4$-alkoxy, nitro or cyano; and $X^-$ is a monobasic acid radical or the equivalent of a polybasic acid radical;

component e) being one or more polyethers of the formula (7)

$R^{10}$—(O—$C_aH_{2a}$)$_b$—$OR^{11}$ (7)

or crown ethers, where, in formula (7)

$R^{10}$ and $R^{11}$ are identical or different and are a straight-chain or branched alkyl radical having from 1 to 16 carbon atoms;

a is an integer from 2 to 6 and b is an integer from 0 to 20, and carrying out the reaction at from 50 to 250° C., removing the compound of the formula (1) formed during the reaction by distillation, and the compound of the formula (2) is fed to the reaction mixture at a rate corresponding to the rate at which the compound of the formula (1) is removed.

Surprisingly, the process according to the invention leads to a clear increase both in the space yield and in the space-time yield. Furthermore, the formation of undesired by-products, secondary products and/or decomposition products is suppressed in an unexpected manner. The formation of these products usually results in a lowering of the yield and can cause a number of work-up problems, such as disposal of polymeric decomposition products or low thermal stability of production residues.

Particularly negative effects are caused by those by-products which for their part lead to readily decomposible products having low decomposition temperatures. An example of this which may be mentioned is the formation of nitrophenols, which are present as phenoxides in the reaction suspension. Such by-products which are very reactive can be triggers for a number of other undesired secondary and consecutive reactions, which preferentially proceed with fluorinated aromatic compounds already formed. In particular, nitrophenoxides have proven problematic since they are able to decompose exothermically, as the example of picric acid salts shows.

A compound of the formula (2) in which Az independently of each other are identical or different and are a radical —F, —Cl, —$NO_2$, —CN, —$CF_3$, —$CCl_3$, —CHO or —CO($C_nH_{2n+1}$), where n is an integer from 1 to 6, in particular from 1 to 4, preferably from 1 to 2, in particular are a radical —Cl, —$NO_2$, —CN, —$CF_3$ or —CHO, can be used successfully in the process according to the invention.

In particular a compound of the formula (2) in which Ar is a phenyl radical or pyridyl radical, in particular a phenyl radical, can be used as a suitable starting compound.

In the compound of the formula (2), y is, as mentioned above, an integer from 1 to 5, in particular from 1 to 4, preferably from 1 to 3, particularly preferably from 1 to 2.

In the process according to the invention, it is possible to use a compound of the formula (2) in which, as already given previously, R independently of one another are identical or different and are H, a straight-chain or branched alkyl radical having from 1 to 10 carbon atoms or a straight-chain or branched alkoxy radical having from 1 to 10 carbon atoms, in particular H, a straight-chain or branched alkyl radical having from 1 to 4 carbon atoms or a straight-chain or branched alkoxy radical having from 1 to 4 carbon atoms, preferably H, an alkyl or alkoxy radical having from 1 to 2 carbon atoms, particularly preferably H.

The alkali metal fluoride used is NaF, KF, RbF, CsF or a mixture thereof, in particular KF or a mixture of KF, RbF and/or CsF.

For a large number of cases, it has proven sufficient to use KF as the alkali metal fluoride. In some cases, mixtures of KF and CsF, which comprise from 1 to 10% by weight of CsF, have proven to be advantageous.

The catalyst used is normally component a) or the mixture of component a) with at least one of components b), c), d) and/or e) in an amount of from 1 to 40% by weight, in particular from 2 to 30% by weight, preferably from 5 to 25% by weight, particularly preferably from 8 to 20% by weight, based on the compound of the formula (2).

In a large number of cases, the reaction can be carried out in the presence of component a) or the mixture of component a) and at least one of components b) and d). In this case, either component a) or the mixture of a)+b) or a)+d) or a)+b)+d) acts as a catalyst.

Component a) is normally one or more quaternary ammonium compounds of the formula (3) in which $R^1$, $R^2$ and $R^3$ are identical or different and are a linear (straight-chain) or branched alkoxypolyoxyalkyl radical of the formula —$(C_mH_{2m}O)_pR^5$, in which $R^5$ is hydrogen or a straight-chain or branched alkyl radical having from 1 to 8 carbon atoms, in particular a straight-chain or branched alkyl radical having from 1 to 8, in particular from 1 to 4, carbon atoms, m is an integer from 1 to 5 and p is an integer from 2 to 10, or a straight-chain or branched alkyl radical having from 1 to 8 carbon atoms; or an unsubstituted or substituted phenyl or naphthyl radical, where the substituents are halogen, $C_1$–$C_4$-alkyl, $C_1$–$C_4$-alkoxy, nitro or cyano, $R^4$ is a straight-chain or branched radical of the formula —$(C_mH_{2m}O)_pR^5$, in which $R^5$ is hydrogen or a straight-chain or branched alkyl radical having from 1 to 8 carbon atoms, in particular a straight-chain or branched alkyl radical having from 1 to 8, in particular from 1 to 4, carbon atoms, m is an integer from 1 to 5 and p is an integer from 2 to 10, and $X^-$ is fluoride, chloride, bromide, $SO_4^{2-}/2$ or hydrogensulfate.

In the straight-chain or branched alkoxypolyoxyalkyl radical of the formula —$(C_mH_{2m}O)_pR^5$ contained in the compound of the formula (3), identical or different alkoxy units may be linked to one another.

The number of straight-chain or branched alkoxypolyoxyalkyl radicals contained in the compound of the formula (3) is preferably 1 or 2.

For the purposes of the present invention, particularly preferred compounds of the formula (3) are dimethyldi(ethoxypolyoxypropyl)ammonium chloride, dimethyldi(ethoxypolyoxypropylmethylether)ammonium chloride, dimethyl(ethoxypolyoxypropyl)(ethoxypolyoxypropylmethylether)ammonium chloride, dimethyldi(ethoxypolyoxyethyl)ammonium chloride, dimethyldi(ethoxypolyoxyethylmethylether)ammonium chloride, dimethyl(ethoxypolyoxyethyl)(ethoxypolyoxyethylmethylether)ammonium chloride, in each case having a mean chain length p of 3, furthermore trimethyl(ethoxypolyoxypropyl)ammonium chloride and trimethyl(ethoxypolyoxypropylmethylether)ammonium chloride, in each case having a mean chain length p of 8, or a mixture of the compounds mentioned above.

The described compounds of the formula (3) can be prepared in a known manner (U.S. Pat. No. 3,123,641; U.S. Pat. No. 3,141,905) from the corresponding ethanolamines, which, after reaction with alkenyl oxides and subsequent quaternization with or without simultaneous etherification, produce the desired compounds in good yields.

In the mixture of component a) and at least one of components b), c), d) and/or e), component a) constitutes from 5 to 95% by weight, in particular from 10 to 90% by weight, preferably from 20 to 80% by weight, of the total mixture which is used as catalyst. The molar ratio of catalyst (component a) or mixture of component a) and at least one of the other components b) to e) to the compound of the formula (2) can be from 1:5 to 1:150, in particular from 1:10 to 1:100, preferably from 1:20 to 1:100. The molar ratio of the compound of the formula (2) to the alkali metal fluoride is 1:(0.5 to 3), in particular 1:(0.8 to 2.5), preferably 1:(0.9 to 1,5).

Component b):

It is possible to use a compound of the formula (4) in which $A^1$, $A^2$, $A^3$, $A^4$, $A^5$, $A^6$, $A^7$ and $A^8$ independently of one another are identical or different and are a straight-chain or branched alkyl or alkenyl, in particular alkyl, having from 1 to 12, in particular from 1 to 8, preferably from 1 to 4, carbon atoms, or cycloalkyl having from 4 to 8, in particular from 5 to 6, carbon atoms. These compounds are of particular interest since they can be prepared in a relatively easy manner starting from the corresponding dialkylamines, dialkenylamines, dicycloalkylamines and secondary amines which contain an alkyl and alkenyl radical, an alkyl and cycloalkyl radical or an alkenyl and cycloalkyl radical.

It is possible to use a compound of the formula (4) in which $A^1A^2=A^3A^4$ or $A^1A^2=A^3A^4=A^5A^6$ or $A^1A^2=A^3A^4=A^5A^6=A^7A^8$. These compounds, in which two or more of the groups $A^1A^2$, $A^3A^4$, $A^5A^6$ and $A^7A^8$ are identical to one another, have relatively good availability.

Examples of alkyl which can be mentioned are methyl, ethyl, n-propyl, i-propyl, n-butyl, i-butyl, n-pentyl, 3-methylbutyl, n-hexyl and 2-ethylhexyl, in particular methyl, ethyl, n-propyl and n-butyl, and examples of alkenyl are allyl, prop-(2)-enyl and n-but-(2)-enyl, and examples of cycloalkyl are cyclopentyl, cyclohexyl, 4-methylcyclohexyl and 4-tert-butylcyclohexyl.

It is also possible to use a compound of the formula (4) in which $A^1=A^2$, $A^3=A^4$, $A^5=A^6$ and/or $A^7=A^8$. These compounds are relatively readily available and therefore of interest.

It is also possible to use a compound of the formula (4) in which $A^1=A^2=A^3=A^4$ or $A^1=A^2=A^3=A^4=A^5=A^6$ or $A^1=A^2=A^3=A^4=A^5=A^6=A^7=A^8$.

These abovementioned compounds, in which four, six or eight of the radicals $A^1$ to $A^8$ are identical, are likewise of interest since they are readily available.

It is also possible to use a compound of the formula (4) in which $A^1A^2$ or $A^1A^2$ and $A^3A^4$ or $A^1A^2$ and $A^3A^4$ and $A^5A^6$ or $A^1A^2$ and $A^3A^4$ and $A^5A^6$ and $A^7A^8$ are linked together, directly or via O or N—$A^9$, to give a saturated or unsaturated ring having 5 or 6 ring members. Accordingly, these compounds contain one, two, three or four of the abovementioned rings.

It is also possible to use a compound of the formula (4) in which $A^1A^2$ or $A^1A2$ and $A^3A^4$ or $A^1A^2$ and $A^3A^4$ and $A^5A^5$ or $A^1A^2$ and $A^3A^4$ and $A^5A^6$ and $A^7A^8$ are joined to give a ring which includes, as ring members, the N atom which carries the respective radicals $A^1$ to $A^8$, optionally O or N—$A^9$ and $CH_2$ groups. In this group, the N atom forms, with the radicals $A^1$ to $A^8$ bonded in each case thereto, for example a hexahydropyridine ring (piperidine ring), tetrahydropyrrole ring (pyrrolidine ring), a hexahydropyrazine ring (piperazine ring) or morpholine ring. Accordingly, these compounds contain one, two, three or four of the above-mentioned rings.

In the compounds of the formulae (3), (4), (5) and (6), $X^-$ is, as already mentioned at the outset, a monobasic acid radical or the equivalent of a polybasic acid radical, in particular the radical of an inorganic mineral acid, an organic carboxylic acid, or an aliphatic or aromatic sulfonic acid.

Normally, use is made of a compound of the formulae (3), (4), (5) and (6) in which $X^-$ is $F^-$, $Cl^-$, $Br^-$, $J^-$, $HF_2^-$, $BF_4^-$, $C_6H_5SO_3^-$, p-$CH_3$—$C_6H_5SO_3^-$, $SO_4^{2-}/2$, $HSO_4^-$, $PF_6^-$ or $CF_3SO_3^-$, in particular $F^-$, $Cl^-$, $Br^-$, $J^-$, $HF_2^-$ or $BF_4^-$.

Component b) can be one or more amidophosphonium salts of the formula (4), in which three radicals $(A^1A^2)N$, $(A^3A^4)N$ and $(A^5A^6)N$ are identical and are a dialkylamino radical having from 1 to 6, in particular from 1 to 4, carbon atoms per alkyl, the dialkylamino radical in particular containing two identical alkyl groups, or is a pyrrolidine, piperidine or morpholine ring, the radical $(A^7A^8)N$ differs from the radicals mentioned above, where $A^7$ and $A^8$ are identical or different and are an alkyl radical having from 1 to 8 carbon atoms or an alkenyl radical having from 1 to 4 carbon atoms, or all four radicals $(A^1A^2)N$, $(A^3A^4)N$, $(A^5A^6)N$ and $(A^7A^8)N$ are identical and are a dialkylamino radical having from 1 to 6, in particular from 1 to 4, preferably from 1 to 2, carbon atoms per alkyl or are a pyrrolidine, piperidine or morpholine ring.

Without laying claim to completeness, the following compounds may be mentioned as examples of compounds of the formula (4):
tetrakis(dimethylamino)phosphonium chloride
tetrakis(diethylamino)phosphonium chloride
tetrakis(dimethylamino)phosphonium bromide
tetrakis(diethylamino)phosphonium bromide
tetrakis(dipropylamino)phosphonium chloride or bromide
tris(diethylamino)(dimethylamino)phosphonium chloride or bromide
tetrakis(dibutylamino)phosphonium chloride or bromide
tris(dimethylamino)(diethylamino)phosphonium chloride or bromide
tris(dimethylamino)(cyclopentylamino)phosphonium chloride or bromide
tris(dimethylamino)(dipropylamino)phosphonium chloride or bromide
tris(dimethylamino)(dibutylamino)phosphonium chloride or bromide
tris(dimethylamino)(cyclohexylamino)phosphonium chloride or bromide
tris(dimethylamino)(diallylamino)phosphonium chloride or bromide
tris(dimethylamino)(dihexylamino)phosphonium chloride or bromide
tris(diethylamino)(dihexylamino)phosphonium chloride or bromide
tris(dimethylamino)(diheptylamino)phosphonium chloride or bromide
tris(diethylamino)(diheptylamino)phosphonium chloride or bromide
tetrakis(pyrrolidino)phosphonium chloride or bromide
tetrakis(piperidino)phosphonium chloride or bromide
tetrakis(morpholino)phosphonium chloride or bromide
tris(piperidino)(diallylamino)phosphonium chloride or bromide
tris(pyrrolidino)(ethylmethylamino)phosphonium chloride or bromide
tris(pyrrolidino)(diethylamino)phosphonium chloride or bromide.

It is also possible to use a mixture of two or more compounds of the formula (4). This proves particularly easy when mixtures of compounds of the formula (4) are used.

The compounds of the formula (4) can, for example, be prepared by reacting phosphorus pentachloride with dialkylamines. The following equation shows the reaction using dimethylamine:

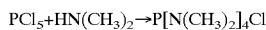

$PCl_5 + HN(CH_3)_2 \rightarrow P[N(CH_3)_2]_4Cl$

It is, however, also possible to react phosphorus pentachloride in stages with various secondary amines, for example dialkylamines, in order to obtain unsymmetrically substituted compounds of the formula (4). Other possibilities of synthesizing compounds of the formula (4) are described by R. Schwesinger et al., Angew. Chem. 103 (1991) 1376 and R. Schwesinger et al., Chem. Ber. 127 (1994) 2435 to 2454.

It has proven successful to use as component c) one or more quaternary ammonium compounds of the formula (5), in which $R^6$, $R^7$ and $R^8$ are identical and are an alkyl radical having from 1 to 4, in particular from 1 to 2, carbon atoms, and $R^9$ is an alkyl radical having from 6 to 24, in particular from 8 to 20, preferably from 10 to 18, carbon atoms, or $R^6$, $R^7$, $R^8$ and $R^9$ are identical and are an alkyl radical having from 1 to 6, in particular from 1 to 4, carbon atoms.

Without laying claim to completeness, the following compounds may be mentioned as individual examples of component c): octadecyltrimethylammonium chloride, hexadecyltrimethylammonium chloride, benzyltrimethylammonium chloride, tetramethylammonium chloride, tetramethylammonium bromide, tetraethylammonium chloride, tetraethylammonium bromide, tetrabutylammonium chloride and tetrabutylammonium bromide. It is also possible to use mixtures of the above compounds.

It has also proven favorable to use as component d) one or more quaternary phosphonium compounds of the formula (6) in which $R^6$, $R^7$ and $R^8$ are identical and are an alkyl radical having from 1 to 4, in particular from 1 to 2, carbon atoms, and $R^9$ is an alkyl radical having from 6 to 24, in particular from 8 to 20, preferably from 10 to 18, carbon atoms, or $R^6$, $R^7$, $R^8$ and $R^9$ are identical and are a phenyl radical or an alkyl radical having from 1 to 6, in particular from 1 to 4, carbon atoms.

Examples of suitable compounds for component d) which may be mentioned are hexadecyltributylphosphonium bromide, stearyltributylphosphonium bromide, tetrabutylphosphonium chloride, tetrabutylphosphonium bromide, tetraoctylphosphonium bromide, tetraphenylphosphonium chloride and tetraphenylphosphonium bromide. It is also possible to use mixtures of the above compounds.

In a number of cases it is advantageous to use as component e) one or more polyethers of the formula (7) in which $R^{10}$ and $R^{11}$ are identical or different and are a straight-chain or branched alkyl radical having from 1 to 8, in particular from 1 to 6, carbon atoms, a is an integer from 2 to 3 and b is an integer from 4 to 14, in particular from 4 to 8, or a crown ether, in particular a polyether of the formula (7), in which $R^{10}$ and $R^{11}$ are identical and are an alkyl radical having from 1 to 8, in particular from 1 to 6, carbon atoms, a is an integer from 2 to 3 and b is an integer from 4 to 14, in particular from 6 to 10.

Interesting mixtures of components a), b), c), d) and e) are those where the weight ratio of a):b) is from 10:1 to 1:10, in particular from 5:1 to 1:5, and components c), d) and e) are present in an amount of from 0 to 25% by weight, in particular from 5 to 20% by weight, based on the mixture.

In a large number of cases, a mixture of components a), b) and d), in which the weight ratio of a): b): d) is (10 to 1):(5 to 0.1): (5 to 0.1), in particular (8 to 2): (3 to 0.5): (3 to 0.5) has proven favorable.

Mixtures of components a) and d), in which the weight ratio of a): d) is from 10:1 to 1:10, in particular from 5:1 to 1:5, can also be used successfully.

The compound of the formula (2) is reacted, as already mentioned at the outset, at from 50 to 250° C., in particular from 70 to 220° C., preferably from 100 to 200° C.

There is a further advantage in that the process according to the invention can be carried out in the absence of a solvent, in particular in the absence of a dipolar aprotic solvent. Examples of dipolar aprotic solvents are dimethyl sulfoxide, dimethyl formamide, diethyl formamide, dimethyl acetamide, diethyl acetamide, hexamethylphosphorus triamide, tetramethylurea, sulfolane (tetramethylene sulfone) and N-methylpyrrolidone. The process according to the invention opens up a way, in an advantageous manner, of dispensing with the use of such solvents, which are normally used in large amounts, based on the starting material. As a result, the reactor volume available for the reaction can be utilized significantly better.

The reaction conditions are chosen such that the fluorinated compound of the formula (1) formed boils and can be distilled off, while the starting compound of the formula (2) added during the reaction does not boil, but remains in the reaction mixture. In a large number of cases, it is advisable to carry out the reaction under a pressure of from 0.001 to 1 bar, in particular from 0.005 to 0.8 bar, preferably from 0.01 to 0.7 bar.

The compound of the formula (1) formed can be distilled off from the reaction mixture batchwise or continuously. It is particularly favorable to distill off continuously the compound of the formula (1) formed from the reaction mixture.

The starting material, i.e. the compound of the formula (2), can be added to the reaction mixture batchwise, i.e. divided into two or more equal or nonequal portions, or the compound of the formula (2) can be added continuously. The continuous addition of the compound of the formula (2) is particularly advantageous.

The fact that the compound of the formula (2), i.e. the starting material, is fed to the reaction mixture at a rate corresponding to the rate at which the end product of the formula (1) is removed, means that the volume of the reaction mixture remains virtually constant and is not subject to relatively large fluctuations. The deviations in the reaction volume during the reaction are normally ±20% by volume, in particular ±10% by volume, based on the reaction mixture.

EXAMPLES

The examples below describe the invention in more detail without limiting it.

Experimental Part

Example 1

Preparation of 2-chloro-4,5-difluoronitrobenzene 836.6 g (14.4 mol) of potassium fluoride are introduced, at 87° C., into a melt of 1680 g (8.0 mol) of 2,4-dichloro-5-fluoronitrobenzene and 202 g (0.3 mol) of methyltris-(methyltetraethoxy)ammonium chloride in a 2.5 liter flat flange flask fitted with distillation bridge and anchor stirrer. 300 g (2.8 mol) of xylene are then added, and the reaction suspension is dried azeotropically by applying a vacuum of 20 mbar and increasing the temperature to 100° C.

The vacuum is reduced to 50 mbar, the reaction temperature is increased to from 128 to 130° C. and the reaction suspension is maintained under these conditions for 11.5 hours. During this time, distillate is continuously removed (from 115 to 118° C. head temperature) and at the same time the corresponding amount of 2,4-dichloro-5-fluoronitrobenzene (total: 1750 g (8.3 mol)) is metered in with thorough stirring.

After the reaction is complete, the reaction suspension is cooled to 25° C. and quickly filtered with suction (25° C.). The removed salts are then washed three times with a total of 450 g of xylene, and the combined organic phases are fractionally distilled.

Yield: 920 g (4.75 mol) of 2-chloro-4,5-difluoronitrobenzene, as well as 1550 g (7.53 mol) of unreacted 2,4-dichloro-5-fluoronitrobenzene; this corresponds to a yield of 29.1%, based on 2,4-dichloro-5-fluoronitrobenzene used, and 54.2%, based on 2,4-dichloro-5-fluoronitrobenzene reacted. Space yield: 368 g/l ; Space-time yield: 32.0 g/l×h (gram/liter×hour).

Comparative Example 1

Preparation of 2-chloro4,5-difluoronitrobenzene 557.7 g (9.6 mol) of potassium fluoride are introduced, at 87° C., into a melt of 1680 g (8.0 mol) of 2,4-dichloro-5-fluoronitrobenzene and 202 g (0.3 mol) of methyltris (methyltetraethoxy)ammonium chloride in a 2.5 liter flat flange flask fitted with distillation bridge and anchor stirrer. 300 g (2.8 mol) of xylene are then added, and the reaction suspension is dried azeotropically by applying a vacuum of 10 mbar and increasing the temperature to 120° C. If 120° C. is reached and no more xylene is distilling over, the distillation bridge is exchanged for a reflux condenser and the reaction suspension is kept at this temperature for 11.5 hours with thorough stirring. The reaction suspension is then cooled to 25° C. and quickly filtered with suction (25° C.). The removed salts are washed three times with a total of 450 g of xylene, and the combined organic phases are fractionated.

Conversion: 69 GC area %; Yield: 420 g (2.17 mol) of 2-chloro-4,5-difluoronitrobenzene, as well as 490 g (2.36 mol) of unreacted 2,4-dichloro-5-fluoronitrobenzene; this corresponds to a yield of 27.1%, based on 2,4-dichloro-5-fluoronitrobenzene used, and 38.3%, based on 2,4-dichloro-5-fluoronitrobenzene reacted. Space yield: 168 g/l; Space-time yield: 14.6 g/l×h.

Example 2

Preparation of 2-fluoronitrobenzene 61.0 g (0.18 mol) of tetrabutylphosphonium bromide and 1007.5 g (17.3 mol) of potassium fluoride are introduced, at 87° C., into a melt of 1575 g (10.0 mol) of 2-chloronitrobenzene and 315.0 g (0.5 mol) of methyltris (methyltetraethoxy)ammonium chloride in a 2.5 liter flat flange flask fitted with distillation bridge and anchor stirrer. 260 g (2.8 mol) of xylene are then added, and the reaction suspension is dried azeotropically by applying a vacuum of 20 mbar and increasing the temperature to 100° C.

The vacuum is reduced to from about 90 to 100 mbar, the reaction temperature is increased to from 158 to 164° C. and the reaction suspension is maintained under these conditions for 10 hours. During this time, distillate is continuously removed (80 to 145° C. head temperature) and at the same time the corresponding amount of 2-chloronitrobenzene (total: 1947 g (12.4 mol)) is metered in with thorough stirring.

After the reaction is complete, the reaction suspension is cooled to 25° C. and quickly filtered with suction (25° C.). The removed salts are then washed three times with a total of 450 g of xylene, and 869.4 g (15.0 mol) of fresh potassium fluoride are added to the resulting mother liquor without further purification. The reaction is then continued as described above. Azeotropic drying (100° C., 20 mbar), then from 157 to 160° C., 90 mbar, semibatch procedure, reaction time 5.5 hours.

The resulting mother liquor is filtered in accordance with the procedure described above, washed with xylene and then, together with the combined distillates, fractionally distilled.

Yield: 1772 g (12.6 mol) of 2-fluoronitrobenzene, as well as 2481 g (15.8 mol) of unreacted 2-chloronitrobenzene; this corresponds to a yield of 42.9%, based on 2-chloronitrobenzene used, and 93.0%, based on 2-chloronitrobenzene reacted. Space yield[1]: 490 g/l; Space-time yield: 50.1 g/l×h; [1] 1227 g (8.7 mol) in the first continuous mixture

Comparative Example 2

Preparation of 2-fluoronitrobenzene 56.7 g (0.17 mol) of tetrabutylphosphonium bromide and 697.2 g (12.0 mol) of potassium fluoride are introduced, at 65° C., into a melt of 1890 g (12.0 mol) of 2-chloronitrobenzene and 113.4 g (0.1 mol) of methyltris (methyltraethoxy)ammonium chloride in a 2.5 l flat flange flask fitted with distillation bridge and impeller stirrer. The reaction mixture is then azeotropically dried with 150 g (1.41 mol) of xylene up to 120° C. under reduced pressure, and the reaction suspension is heated to 170° C. and maintained at this temperature for 21 hours with thorough stirring.

Conversion: 79 GC area %; Yield: 1085 g (7.7 mol) of 2-fluoronitrobenzene, as well as 315 g (2.0 mol) of unreacted 2-chloronitrobenzene; this corresponds to a yield of 64.2%, based on 2-chloronitrobenzene used, and 77.0%, based on 2-chloronitrobenzene reacted. Space yield: 434 g/l; Space-time yield: 20.7 g/l×h.

Example 3

Preparation of 2-chloro-6-fluorobenzaldehyde 290 g (5.0 mol) of potassium fluoride are introduced, at 80° C., into a melt of 875 g (5.0 mol) of 2,6-dichlorobenzaldehyde and 87 g (0.13 mol) of methyltris-(methyltetraethoxy)ammonium chloride in a 2.5 liter flat flange flask fitted with distillation bridge and impeller stirrer. 22 g (0.055 mol) of tetrakis(diethylamino)phosphonium bromide are then introduced and 66 g (0.6 mol) of chlorobenzene are added, and the reaction suspension is dried azeotropically by applying a vacuum of 20 mbar and increasing the temperature to an internal temperature of 127° C.

After the azeotropic drying, the vacuum is reduced to 55 mbar, the reaction temperature is increased to an internal temperature of from 168 to 170° C. and the reaction suspension is maintained under these conditions for 20 hours. During this time, distillate is continuously removed (120 to 130° C. head temperature) and at the same time a further 263 g (1.5 mol) of 2,6-dichlorobenzaldehyde are metered in over the course of the reaction. 560 g of distillate are produced during the 20 hours.

After the reaction is complete, 500 ml of chlorobenzene are added to the remaining reaction suspension at 100° C. with stirring, and the mixture is quickly filtered with suction at 25° C. The removed salts are then washed three times with a total of 500 ml of chlorobenzene, and all of the organic phases are purified by fractional distillation.

Yield: 443 g (2.79 mol) of 2-chloro-6-fluorobenzaldehyde as well as 446 g (2.55 mol) of unreacted 2,6-dichlorobenzaldehyde; this corresponds to a yield of 42.9% of theory, based on 2,6-dichlorobenzaldehyde used, and 70.6% of theory, based on 2,6-dichlorobenzaldehyde reacted. In addition, only 29 g (0.20 mol) of 2,6-difluorobenzaldehyde are isolated after fractionation (3.1 mol %). Space yield: 177 g/l; Space-time yield: 8.9 g/l×h.

Comparative Example 3

Preparation of 2-chloro-6-fluorobenzaldehyde 290 g (5 mol) of potassium fluoride are introduced, at from about 80 to 85° C., into a melt of 875 g (5.0 mol) of 2,6-dichlorobenzaldehyde and 87 g (0.13 mol) of methyltris (methyltetraethoxy)ammonium chloride in a 2.5 liter flat flange flask fitted with distillation bridge and impeller stirrer. 22 g (0.055 mol) of tetrakis(diethylamino)phosphonium bromide are then introduced, and then 66 g (0.6 mol) of chlorobenzene are added and the reaction suspension is dried azeotropically by appling a vacuum of 20 mbar and increasing the temperature to an internal temperature of 127° C. As soon as the internal temperature exceeds 127° C. and no more chlorobenzene distils over, the vacuum is lifted and the distillation bridge exchanged for a reflux condenser.

The mixture is stirred under protective gas at 170° C. for 21 hours. The reaction suspension is then cooled to 60° C. and quickly filtered with suction. The removed salts are washed five times with a total of 500 ml of chlorobenzene, and the combined organic phases are fractionated.

Conversion: 71.5 GC area %; Yield: 314 g (1.98 mol) of 2-chloro-6-fluorobenzaldehyde, as well as 225 g (1.29 mol) of unreacted 2,6-dichlorobenzaldehyde; this corresponds to a yield of 39.6% of theory, based on 2,6-dichlorobenzaldehyde used, and 53.4% of theory, based on 2,6-dichlorobenzaldehyde reacted. In addition, 194 g (0.73 mol) of 2,6-difluorobenzaldehyde are isolated after fractionation (14.6 mol %). Space yield: 126 g/l; Space-time yield: 6.0 g/l×h.

Comparative Example 3a

Preparation of 2-chloro-6-fluorobenzaldehyde

The procedure is as in Comparative Example 3, but 875 g (5.0 mol) of 2,6-dichlorobenzaldehyde is reacted with 232 g (4 mol) of potassium fluoride, corresponding to 80 mol %. T he conversion is monitored by GC and the reaction is stopped after just 18 hours because there is no further conversion. The product is isolated by fractional distillation.

Conversion: 60.5 GC area %; Yield: 282 g (1.77 mol) of 2-chloro-6-fluorobenzaldehyde, as well as 346 g (1.98 mol) of unreacted 2,6-dichlorobenzaldehyde; this corresponds to a yield of 35.4% of theory, based on 2,6-dichlorobenzaldehyde used and 58.6% of theory, based on 2,6-dichlorobenzaldehyde reacted. In addition, 54.3 g (0.38 mol) of 2,6-difluorobenzaldehyde are isolated after fractionation (7.6 mol %). Space yield: 113 g/l; Space-time yield: 6.3 g/l×h.

Example 4

Preparation of 4-chloro-2,3-difluoronitrobenzene 1047.4 g (18.03 mol) of potassium fluoride are introduced, at 68° C., into a melt of 1679.2 g (8.0 mol) of 2,4-dichloro-3-fluoronitrobenzene and 335.8 g (0.53 mol) of methyltris(methyltetraethoxy)ammonium chloride in a 2.5 liter flat flange flask fitted with distillation bridge and anchor stirrer. 205 g (1.93 mol) of xylene are then added, and the reaction suspension is dried azeotropically by applying a vacuum of 20 mbar and increasing the temperature to 130° C.

The vacuum is reduced to 30 mbar, the reaction temperature is increased to from 137 to 145° C. and the reaction suspension is maintained under these conditions for 4.5 hours. During this time, distillate is continuously removed (122 to 132° C. head temperature) and at the same time the corresponding amount of 2,4-dichloro-3-fluoronitrobenzene (total: 1050 g (5.0 mol), is metered in with thorough stirring.

After the reaction is complete, the reaction supension is cooled to 25° C. and quickly filtered with suction (25° C.). The removed salts are then washed three times with a total of 450 g of xylene, and the combined organic phases are fractionally distilled.

Yield: 655 g (3.38 mol) of 4-chloro-2,3-difluoronitrobenzene, as well as 1463 g (6.97 mol) of unreacted 2,4-dichloro-3-fluoronitrobenzene; this corresponds to a yield of 26.0%, based on 2,4-dichloro-3-fluoronitrobenzene used, and 56.1%, based on 2,4-dichloro-3-fluoronitrobenzene reacted. Space yield: 262 g/l; Space-time yield: 58.2 g/l×h.

Example 5

Preparation of 2-chloro-4,5-difluoronitrobenzene 836.6 g (14.4 mol) of potassium fluoride are introduced, at 87° C., into a melt of 1680 g (8.0 mol) of 2,4-dichloro-5-fluoronitrobenzene and 336.0 g (0.53 mol) of methyltris (methyltetraethoxy)ammonium chloride in a 2.5 liter flat flange flask fitted with distillation bridge and anchor stirrer. 150 g (2.8 mol) of xylene are then added, and the reaction suspension is dried azeotropically by applying a vacuum of 20 mbar and increasing the temperature to 100° C.

The vacuum is reduced to 30 mbar, the reaction temperature is increased to from 128 to 130° C. and the reaction suspension is maintained under these conditions for 6.5 hours. During this time, distillate is continuously removed (110 to 115° C. head temperature) and at the same time the corresponding amount of 2,4-dichloro-5-fluoronitrobenzene (total: 1200 g (5.7 mol)) is metered in with thorough stirring.

After the reaction is complete, the reaction suspension is cooled to 25° C. and quickly filtered with suction. The removed salts are then washed three times with a total of 450 g of xylene, and 836.6 g (14.4 mol) of fresh potassium fluoride are added to the resulting mother liquor without further purification. The reaction is then continued as described above. Azeotropic drying (100° C., 20 mbar), then from 128 to 130° C., 30 mbar, semibatch procedure, reaction time 5.5 hours.

The resulting mother liquor is filtered in accordance with the procedure described above, washed with xylene and then, together with the combined distillates, fractionally distilled.

Yield: 1112 g (5.8 mol) of 2-chloro-4,5-difluoronitrobenzene, as well as 1150 g (5.5 mol) of unreacted 2,4-dichloro-5-fluoronitrobenzene; this corresponds to a yield of 31.4%, based on 2,4-dichloro-5-fluoronitrobenzene used, and 44.6%, based on 2,4-dichloro-5-fluoronitrobenzene reacted. Space yield: 444.8 g/l; Space-time yield: 38.7 g/l×h.

What is claimed is:

1. A process for the preparation of fluorinated compounds of the formula (1)

$$Az_xArF_w Cl_{(y-w)}R_z \qquad (1)$$

in which Az independently of one another are identical or different and are a radical —F, —Cl, —Br, —NO$_2$, —CN, —CF$_3$, —CCl$_3$, —CHO, —CO(C$_n$H$_{2n+1}$), where n is an integer from 1 to 10, —COX or —SO$_2$X, where X is F, Cl or Br, x is an integer from 1 to 3, Ar is a phenyl radical, pyridyl radical or naphthyl radical, w is an integer from 1 to y, y is an integer from 1 to 5, R independently of one another are identical or different and are H, a straight-chain or branched alkyl radical having from 1 to 10 carbon atoms or a straight-chain or branched alkoxy radical having from 1 to 10 carbon atoms, z is an integer from 1 to 5, where (x+y+z) is the number of all substitutable valences on the radical Ar, which comprises reacting a compound of the formula (2)

$$Az_xArCl_yR_z \qquad (2),$$

in which Az, x, Ar, y, R, z and (x+y+z) are as defined for formula 1, with an alkali metal fluoride or a mixture of alkali metal fluorides in the presence of a component a) or a mixture of component a) and at least one of components b), c), d) and e), component a) being one or more quaternary ammonium compounds of the formula (3)

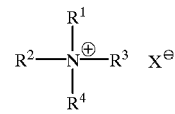

$$R^2-\overset{R^1}{\underset{R^4}{\overset{|}{N^\oplus}}}-R^3 \quad X^\ominus \qquad (3)$$

in which

R$^1$, R$^2$ and R$^3$ are identical or different and are a straight-chain or branched radical of the formula —(C$_m$H$_{2m}$O)$_p$R$^5$, in which R$^5$ is hydrogen or a straight-chain or branched alkyl radical having from 1 to 16 carbon atoms, m is an integer from 1 to 10 and p is a number from 1 to 15; or a straight-chain or branched alkyl radical having from 1 to 30 carbon atoms;

or an unsubstituted phenyl or naphthyl radical; or a substituted phenyl or naphthyl radical where the substituents are halogen, C$_1$–C$_4$-alkyl, C$_1$–C$_4$-alkoxy, nitro or cyano;

R$^4$ is a straight-chain or branched radical of the formula —(C$_m$H$_{2m}$O)$_p$R$^5$; and X$^\ominus$ is a monobasic acid radical or the equivalent of a polybasic acid radical, component b) being one or more amidophosphonium salts of the formula (4)

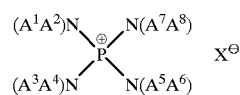

$$(A^1A^2)N \diagdown \overset{\oplus}{P} \diagup N(A^7A^8) \quad X^\ominus \qquad (4)$$
$$(A^3A^4)N \diagup \quad \diagdown N(A^5A^6)$$

in which A$^1$, A$^2$, A$^3$, A$^4$, A$^5$, A$^6$, A$^7$, A$^8$ independently of one another are identical or different and are a straight-chain or branched alkyl or alkenyl having from 1 to 12 carbon atoms, cycloalkyl having from 4 to 8 carbon atoms, an aryl having from 6 to 12 carbon atoms, an aralkyl having from 7 to 12 carbon atoms, or A$^1$A$^2$, A$^3$A$^4$, A$^5$A$^6$ and A$^7$A$^8$ independently of one another are identical or different and are bonded together, directly or via O or N—A$^9$, to give a ring having from 3 to 7 ring members, A$^9$ is an alkyl having from 1 to 4 carbon atoms and X$^-$ is a monobasic acid radical or the equivalent of a polybasic acid radical, component c) being one or more quaternary ammonium compounds of the formula (5)

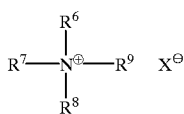
(5)

in which
R⁶, R⁷, R⁸ and R⁹ are identical or different and are a straight-chain or branched alkyl radical having from 1 to 22 carbon atoms; or an unsubstituted or substituted aryl radical or a $C_1$–$C_4$-alkylaryl radical, where aryl is phenyl or naphthyl, and said substituents are halogen, $C_1$–$C_4$-alkyl, $C_1$–$C_4$-alkoxy, nitro or cyano; and X⁻ is a monobasic acid radical or the equivalent of a polybasic acid radical;
component d) being one or more quaternary phosphonium compounds of the formula (6)

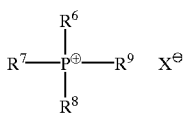
(6)

in which
R⁶, R⁷, R⁸ and R⁹ are identical or different and are a linear or branched alkyl radical having from 1 to 22 carbon atoms; or an unsubstituted or substituted aryl radical or a $C_{1-C_4}$-alkylaryl radical, where aryl is phenyl or naphthyl, and said substituents are halogen, $C_1$–$C_4$-alkyl, $C_1$–$C_4$-alkoxy, nitro or cyano; and X⁻ is a monobasic acid radical or the equivalent of a polybasic acid radical; component e) being one or more polyethers of the formula (7)

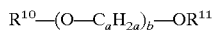
$R^{10}$—$(O$—$C_aH_{2a})_b$—$OR^{11}$ (7)

or crown ethers, where, in formula (7)
R¹⁰ and R¹¹ are identical or different and are a straight-chain or branched alkyl radical having from 1 to 16 carbon atoms;
a is an integer from 2 to 6 and
b is an integer from 0 to 20, and carrying out the reaction at from 50 to 250° C., removing the compound of the formula (1) formed during the reaction by distillation, and the compound of the formula (2) is fed to the reaction mixture at a rate corresponding to the rate at which the compound of the formula (1) is removed.

2. The process as claimed in claim 1, wherein a compound of the formula (2) in which Az independently of one another are identical or different and are a radical —F, —Cl, —NO₂, —CN, —CF₃, —CCl₃, —CHO or —CO($C_nH_{2n+1}$), where n is an integer from 1 to 6 is used.

3. The process as claimed in claim 1, wherein a compound of the formula (2) in which Ar is a phenyl radical or pyridyl radical is used.

4. The process as claimed in claim 1, wherein a compound of the formula (2) in which y is an integer from 1 to 3 is used.

5. The process as claimed in claim 1, wherein a compound of the formula (2) in which R is H, a straight-chain or branched alkyl radical having from 1 to 4 carbon atoms or a straight-chain or branched alkoxy radical having from 1 to 4 carbon atoms is used.

6. The process as claimed in claim 1, wherein the alkali metal fluoride used is NaF, KF, RbF, CsF or a mixture thereof.

7. The process as claimed in claim 1, wherein component a) or the mixture of component a) with at least one of components b), c), d) and/or e) is used in an amount of from 1 to 40% by weight, based on the compound of the formula (2).

8. The process as claimed in claim 1, wherein the reaction is carried out in the presence of component a) or the mixture of component a) and at least one of components b) and d).

9. The process as claimed in claim 1, wherein component a) is one or more quaternary ammonium compounds of the formula (3) in which
R¹, R² and R³ are identical or different and are a straight-chain or branched radical of the formula —($C_mH_{2m}O$)$_pR^5$, in which R⁵ is hydrogen or a straight-chain or branched alkyl radical having from 1 to 8 carbon atoms, m is an integer from 1 to 5 and p is an integer from 2 to 10; or a straight-chain or branched alkyl radical having from 1 to 18 carbon atoms; or an unsubstituted or substituted phenyl or naphthyl radical, where the substituents are halogen, $C_1$–$C_4$-alkyl, $C_1$–$C_4$-alkoxy, nitro or cyano;
R⁴ is a straight-chain or branched alkoxypolyoxyalkyl radical of the formula —($C_mH_{2m}O$)$_pR^5$, in which R⁵ is hydrogen or a straight-chain or branched alkyl radical having from 1 to 8 carbon atoms, m is an integer from 1 to 5 and p is an integer from 2 to 10; and
X⁻ is fluoride, chloride, bromide, $SO_4^{2-}/2$ or hydrogensulfate.

10. The process as claimed in claim 1, wherein dimethyldi(ethoxypolyoxypropyl)ammonium chloride, dimethyldi(ethoxypolyoxypropylmethylether) ammonium chloride, dimethyl(ethoxypolyoxypropyl) (ethoxypolyoxypropylmethylether)ammonium chloride, dimethyldi(ethoxypolyoxyethyl)ammonium chloride, dimethyldi(ethoxypolyoxyethylmethylether) ammonium chloride, dimethyl(ethoxypolyoxyethyl) (ethoxypolyoxyethylmethylether)ammonium chloride, in each case having a mean chain length p of 3, or trimethyl(ethoxypolyoxypropyl)ammonium chloride or trimethyl(ethoxypolyoxypropylmethylether) ammonium chloride, in each case having a mean chain length p of 8, or a mixture of the compounds mentioned above is used as component a).

11. The process as claimed in claim 1, wherein component b) is one or more amidophosphonium salts of the formula (4)

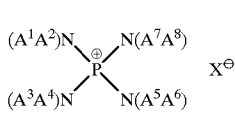
(4)

in which three radicals (A¹A²)N, (A³A⁴)N and (A⁵A⁶)N are identical and are a dialkylamino radical having from 1 to 6, carbon atoms per alkyl or are a pyrrolidine, piperidine or morpholine ring, the radical (A⁷A⁸)N differs from the radicals mentioned above, where A⁷ and A⁸ are identical or different and are an alkyl radical having from 1 to 8 carbon atoms or alkenyl radical having from 1 to 4 carbon atoms, or all four radicals (A¹A²)N, (A³A⁴)N, (A⁵A⁶)N and (A⁷A⁸)N are identical and are a dialkylamino radical having from 1 to 6, carbon atoms per alkyl or are a pyrrolidine, piperidine or morpholine ring.

12. The process as claimed in claim 1, wherein component c) is one or more quaternary ammonium compounds of the formula (5) in which $R^6$, $R^7$ and $R^8$ are identical and are an alkyl radical having from 1 to 4, and $R^9$ is an alkyl radical having from 6 to 24, or $R^6$, $R^7$, $R^8$ and $R^9$ are identical and are an alkyl radical having from 1 to 6, carbon atoms.

13. The process as claimed in claim 1, wherein component d) is one or more quaternary phosphonium compounds of the formula (6) in which $R^6$, $R^7$ and $R^8$ are identical and are an alkyl radical having from 1 to 4, carbon atoms, and $R^9$ is an alkyl radical having from 6 to 24, carbon atoms, or $R^6$, $R^7$, $R^8$ and $R^9$ are identical and are a phenyl radical or alkyl radical having from 1 to 6, carbon atoms.

14. The process as claimed in claim 1, wherein component e) is one or more polyethers of the formula (7) in which $R^{10}$ and $R^{11}$ are identical or different and are a straight-chain or branched alkyl radical having from 1 to 8 carbon atoms, a is an integer from 2 to 3 and b is an integer from 4 to 14, or a crown ether.

15. The process as claimed in claim 7, wherein component a) or the mixture of component a) with at least one of components b), c), d) and/or e) is used in an amount of from 2 to 30% by weight, based on the compound of the formula (2).

16. The process as claimed in claim 7, wherein component a) or the mixture of component a) with at least one of components b), c), d) and/or e) is used in an amount of from 5 to 20% by weight, based on the compound of the formula (2).

17. The process as claimed in claim 11, wherein component b) is one or more amidophosphonium salts of the formula (4)

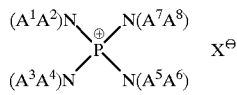

(4)

in which three radicals $(A^1A^2)N$, $(A^3A^4)N$ and $(A^5A^6)N$ are identical and are a dialkylamino radical having from 1 to 4, carbon atoms per alkyl or are a pyrrolidine, piperidine or morpholine ring, the radical $(A^7A^8)N$ differs from the radicals mentioned above, where $A^7$ and $A^8$ are identical or different and are an alkyl radical having from 1 to 8 carbon atoms or alkenyl radical having from 1 to 4 carbon atoms, or all four radicals $(A^1A^2)N$, $(A^3A^4)N$, $(A^5A^6)N$ and $(A^7A^8)N$ are identical and are a dialkylamino radical having from 1 to 4, carbon atoms per alkyl or are a pyrrolidine, piperidine or morpholine ring.

18. The process as claimed in claim 12, wherein component c) is one or more quaternary ammonium compounds of the formula (5) in which $R^6$, $R^7$ and $R^8$ are identical and are an alkyl radical having from 1 to 2, carbon atoms, and $R^9$ is an alkyl radical having from 8 to 20, carbon atoms, or $R^6$, $R^7$, $R^8$ and $R^9$ are identical and are an alkyl radical having from 1 to 4, carbon atoms.

19. The process as claimed in claim 18, wherein $R^9$ is an alkyl radical having from 10 to 18, carbon atoms.

20. The process as claimed in claim 13, wherein component d) is one or more quaternary phosphonium compounds of the formula (6) in which $R^6$, $R^7$ and $R^8$ are identical and are an alkyl radical having from 1 to 2, carbon atoms, and $R^9$ is an alkyl radical having from 8 to 20 carbon atoms, or $R^6$, $R^7$, $R^8$ and $R^9$ are identical and are a phenyl radical or alkyl radical having from 1 to 4, carbon atoms.

21. The process as claimed in claim 20, wherein $R^9$ is an alkyl radical having from 10 to 18, carbon atoms.

* * * * *